United States Patent [19]

Arpin

[11] Patent Number: 4,702,231

[45] Date of Patent: Oct. 27, 1987

[54] PORTABLE HEART MASSAGE APPARATUS

[76] Inventor: Pierre P. Arpin, 1347 Highland Ct., Milpitas, Calif. 95035

[21] Appl. No.: 789,500

[22] Filed: Oct. 21, 1985

[51] Int. Cl.⁴ ............................................. A61H 31/00
[52] U.S. Cl. ........................................ 128/28; 128/53; 128/38
[58] Field of Search ............... 128/28, 30, 30.2, 38–40, 128/53, 55; 417/415

[56] References Cited

U.S. PATENT DOCUMENTS

| 1,179,129 | 4/1916 | Maxam | 128/38 |
| 1,898,652 | 2/1933 | Williams | 128/38 |
| 2,222,811 | 11/1940 | Dinesen | 417/415 |
| 3,234,934 | 2/1966 | Woodward | 128/53 |
| 3,425,409 | 2/1969 | Issason | 128/28 |
| 3,509,899 | 5/1970 | Hewson | 128/28 |

Primary Examiner—Richard J. Apley
Assistant Examiner—J. Welsh
Attorney, Agent, or Firm—John J. Leavitt

[57] ABSTRACT

Presented is an apparatus operable to compress the chest of a person whose heart has stopped so as to initiate and maintain the flow of blood through the body during a cardiopulmonary resuscitation procedure. Structurally, the apparatus includes a carrying case containing a motor for driving an actuator mechanism for actuating a pair of hydraulic cylinders connected together in a "slave" arrangement. The "slave" cylinder is mounted on a platform adapted to be strapped to the chest of the victim, with the "slave" cylinder having a ram that pushes rhythmically against the sternum to squeeze the heart between the sternum and backbone of the victim. A breathing apparatus (pulmonary resuscitator) may be driven by the motor in concert with the compression function to inflate the victim's lungs with air and thus supply oxygen to the blood stream.

2 Claims, 12 Drawing Figures

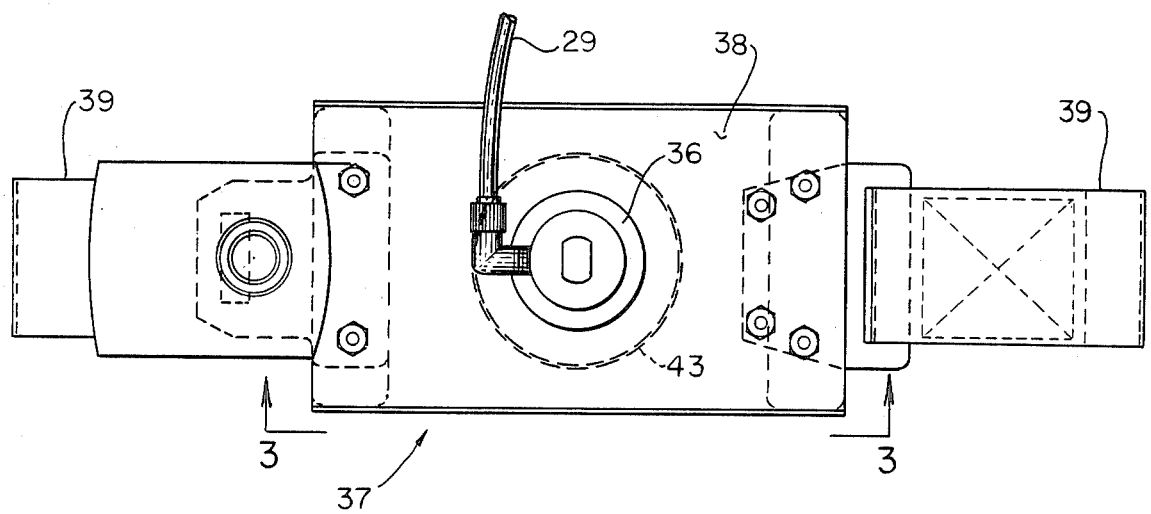
FIG. 2
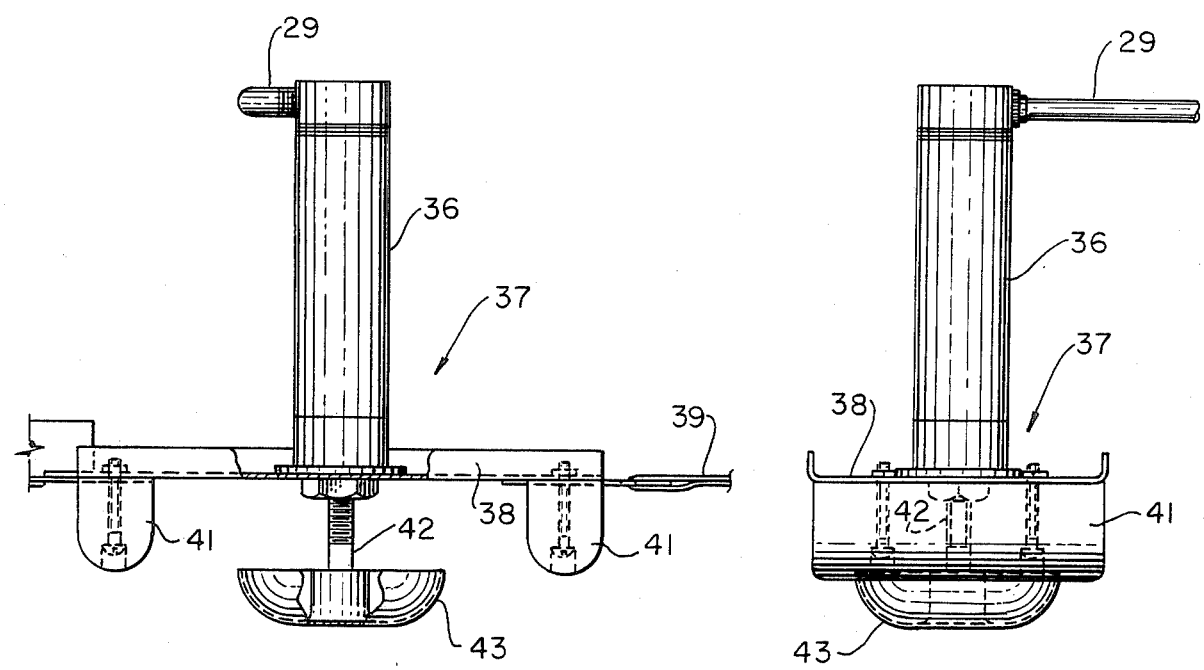
FIG. 3
FIG. 4

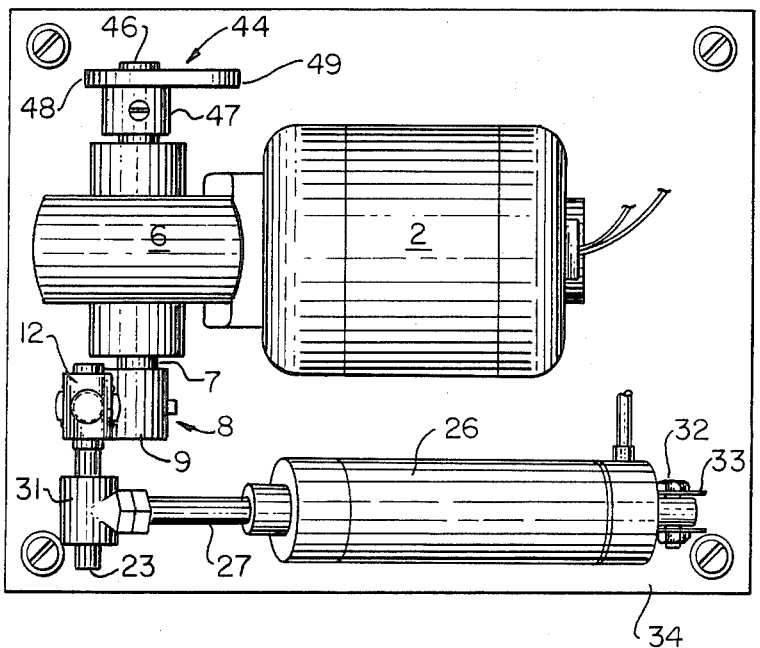
FIG. 5
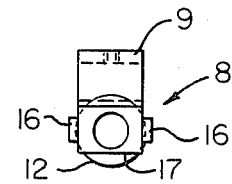
FIG. 9
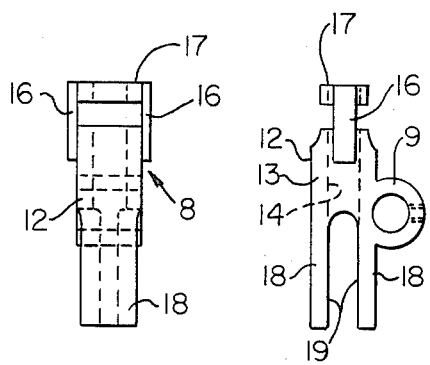
FIG. 7   FIG. 8
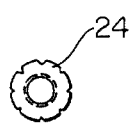 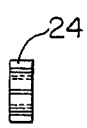
FIG. 10   FIG. 11
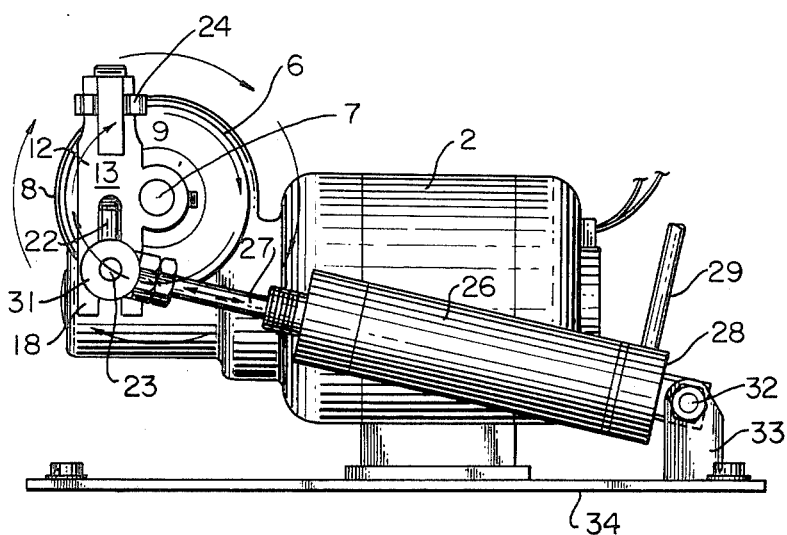
FIG. 6
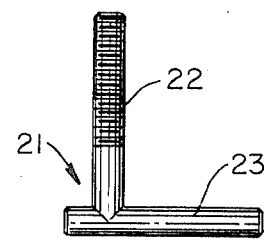
FIG. 12

PORTABLE HEART MASSAGE APPARATUS

BACKGROUND OF THE INVENTION

1. Field of the Invention.

This invention relates to cardiopulmonary resuscitation, and particularly to a portable apparatus applicable to massage the heart of a person whose heart has stopped beating.

2. Description of the Prior Art.

It is believed the prior art relating to this invention may be found in Class 128, sub-classes 90 and 28; and Class 434, sub-class 265.

A search for prior art has revealed the existence of U.S. Pat. Nos. 1,918,546; 2,036,371; 2,484,306; 3,254,645 and 4,338,924.

U.S. Pat. No. 1,918,546 is directed to an artificial respirator, and does not appear to include apparatus for massaging the heart.

U.S. Pat. No. 2,036,371 is also directed to artificial resuscitation, and teaches a device that applies pressure downwardly and forwardly and then upwardly and rearwardly to inflate the lungs.

U.S. Pat. No. 2,484,306 relates to respirators used to revive a drowning victim, or a victim whose breathing has been interrupted. This patent, as with U.S. Pat. No. 1,918,546, describes a structure including a framework which supports a ram that is spring-pressed in an upward direction, but which may be forced downwardly against the spring pressure by a cam operated by rotation of a handle, to effect compression and expansion of the lungs.

U.S. Pat. Nos. 3,254,645 and 4,338,924 are the only two patents found that relate specifically to heart massage devices. However, both these patents teach structures that are significantly different from my invention in both structure and mode of operation.

In one aspect, this invention relates to heart massage, and in another aspect, functions to activate a respirator to provide for both circulation of blood and oxygenation of the blood being circulated.

It is well known that the heart and lungs work in unison to circulate and oxygenate the blood stream. The performance of both these functions simultaneously has been labeled cardiopulmonary resuscitation. The term has been abbreviated to CPR, and classes in CPR are regularly given throughout the United States. The term "cardio" of course refers to the heart, and "pulmonary" refers to the lungs. CPR of course includes mouth-to-mouth breathing, but may also include artificial respiration as performed by a mechanical respirator. Whether respiration is assisted by mouth-to-mouth breathing, or by a mechanical respirator, it is apparent that respiration aid should be accomplished in concert with chest compressions to massage the heart when the heart has stopped beating. Accordingly, one of the objects of the present invention is the provision of a mechanical heart massage apparatus that selectively operates in conjunction with or without artificial respiration efforts.

When a person's heart stops beating, blood stops flowing in the body, particularly to the brain, and it is known that the lack of a supply of oxygen to the brain for only a very short time can cause permanent damage to that organ. It is therefore imperative that heart massage be initiated without delay. Accordingly, another object of the invention is the provision of a heart massage apparatus that can be applied to a person and activated in an extremely short interval of time.

Literature on the subject of CPR is explicit regarding the repetition rate of chest compressions for adults, children and infants. The diffuculty is that few people in the position of a rescurer have read the literature, and fewer people have practiced CPR so as to learn the desirable techniques. Accordingly, a still further object of the invention is the provision of a heart massage apparatus which may be easily and quickly applied to a victim of any size and age, and which may just as quickly and easily be adjusted to accord with the recommended chest compression rate and extent for the particular victim involved.

Victims to whom heart massage has been administered by hand sometimes receive injuries because of poor technique including improper placement of hands, improper application of pressure, distribution of pressure over too large an area, insufficient chest compression or too much chest compression. Accordingly, another object of the invention is the provision of an apparatus which may quickly be strapped onto a victim's chest at precisely the proper position, and adjusted to effect just the right amount of chest compression at the recommended repetition rate.

Heart massage is conventionally administered with the victim lying on his back on a hard surface. The literature on the subject cautions against administering heart massage while the victim is lying on a soft surface, such as a bed. The reason for this caution is that heart massage proceeds by compression or squeezing of the heart between the sternum (breast bone) and the back bone or spine. It is said that if the back bone is not supported on a hard surface, i.e., one that will not yield, then compression of the chest cannot be effected. It is therefore an important object of this invention to provide a heart massage apparatus that will function to compress the chest even if the victim is lying on a soft support and continue to apply rhythmic heart massage even while the victim is transported or moved from one location to another.

The amount or extent of chest compression varies depending on the size and age of the victim. Thus, for most adults, the recommended chest compression is about 1½ to 2 inches. For a child, ¾" to 1½", and for an infant ½" to ¾". The repetition rate of chest compression also varies, depending on size, age, and whether there are one or two rescuers involved in the procedure. Where a single rescuer is involved with an adult victim, the recommended repetition rate is 80 compressions per minute. If two rescuers are present, the rate drops to 60 per minute. For a child, 80-100 compressions per minute are recommended, while for an infant 100 compressions per minute are recommended. Obviously, even where two rescuers are present, given the trauma and anxiety present in the circumstances, it is most difficult for a rescuer to apply the requisite amount of pressure to achieve adequate chest compression and count the number of compressions per minute. Accordingly, it is a provision of the present invention to provide a heart massage apparatus that may be easily applied to any victim of any size, and which may easily be adjusted to provide the requisite number of chest compressions of the appropriate extent.

In the administration of heart massage, it is important that, once started, there be no more than a five second interruption in the procedure. It is also important that the application of pressure be rhythmic and regular, and that either mouth-to-mouth breathing accompany the heart massage, or that some form of artificial respiration be provided. It is therefore another object of this invention to provide a heart massage apparatus that, once applied and started, will continue operating indefinitely and independently of the rescuer in a regular and rhythmic repetition rate, thus permitting a single rescuer to apply mouth-to-mouth breathing in unison with the heart massage apparatus.

Once a victim's heart commences beating on its own after heart massage, it is important to monitor the victim carefully so as to be ready to resume heart massage should the heart falter again. Accordingly, another object of this invention is the provision of a heart massage apparatus that is portable, that may be left strapped to the victim ready to resume heart massage if the need arises, yet which constitutes no impediment to other ministrations that might be imposed on the victim by other life support systems, such as a respirator or oxygen tent.

Rescue personnel are often ordinary people with no special training who find themselves in the predicament of having to render aid. Where the aid required is heart massage, the anxiety and apprehension of the rescuer may be particularly acute. Coupling this anxiety and apprehension with lack of knowledge can have a devastating effect not only on the rescuer but also on the victim. Accordingly, another object of this invention is to provide a heart massage apparatus which itself guides the rescuer to make the proper adjustments of the apparatus in relation to the victim to which it is being applied.

The invention possesses other objects and features of advantage, some of which, with the foregoing, will be apparent from the following description and the drawings. It is to be understood however that the invention is not limited to the embodiment illustrated and described, since it may be embodied in various forms within the scope of the appended claims.

SUMMARY OF THE INVENTION

In terms of broad inclusion, the heart massage apparatus of the invention comprises an apparatus which may be packed in a suitcase type carrying case for ease of portability and for assurance that all aspects of the apparatus are present and ready for use at an instants notice. The carrying case supports an electrically powered motor and a battery pack, the arrangement being such that the apparatus may be powered from either a direct current or alternating current power source. The motor drives a gear reduction device which in turn is connected to an actuator which drives a master or primary hydraulic cylinder also contained within the carrying case. The apparatus includes a "slave" hydraulic cylinder connected to one end of a long hydraulic tube from the master cylinder. The "slave" cylinder is mounted on a breast plate adapted to be releasably strapped to the victim's chest to position the ram from the "slave" cylinder over the sternum of the victim. An appropriate pad or "shoe" is mounted on the ram to impose a cushioned repetitive compressive force on the sternum when the apparatus is activated. Means are provided on the actuator for connection to an artificial respirator device to drive the respirator in timed sequence with the heart massage apparatus. means are also provided on the actuator to adjust the length and repetition rate of each stroke.

BRIEF DESCRIPTION OF THE DRAWINGS

FIG. 2 is a plan view of the breast plate and "slave" cylinder, and illustrating the quick release strap means by which the breast plate is releasably attached to the victim.

FIG. 3 is an edge view of the breast plate assembly, showing the pressure-applying ram extended in a pressure-applying attitude. The view is taken in the direction indicated by the arrows 3—3 in FIG. 2.

FIG. 4 is an end view of the breast plate assembly of FIG. 3.

FIG. 5 is a fragmentary plan view of a portion of the carrying case illustrating the drive motor, gear reduction and master or primary cylinder assembly.

FIG. 6 is a fragmentary side elevational view of the actuator mechanism and master cylinder and illustrating the adjustment means for controlling the length of stroke of the pressure-applying ram, and its repetition rate.

FIG. 7 is a front elevational view of the stroke control adjustment mechanism apart from the apparatus.

FIG. 8 is a side elevational view of the stroke control adjustment mechanism apart from the apparatus.

FIG. 9 is a plan view of the stroke control adjustment mechanism apart from the apparatus.

FIG. 10 is a plan view of the stroke control adjustment thumb wheel.

FIG. 11 is an edge view of the thumb wheel of FIG. 10.

FIG. 12 is a side elevational view of the master cylinder ram journal and control spindle which cooperate with the thumb wheel to selectively adjust the stroke of the master cylinder, and the repetition rate thereof.

DESCRIPTION OF THE PREFERRED EMBODIMENT

Figure 1:
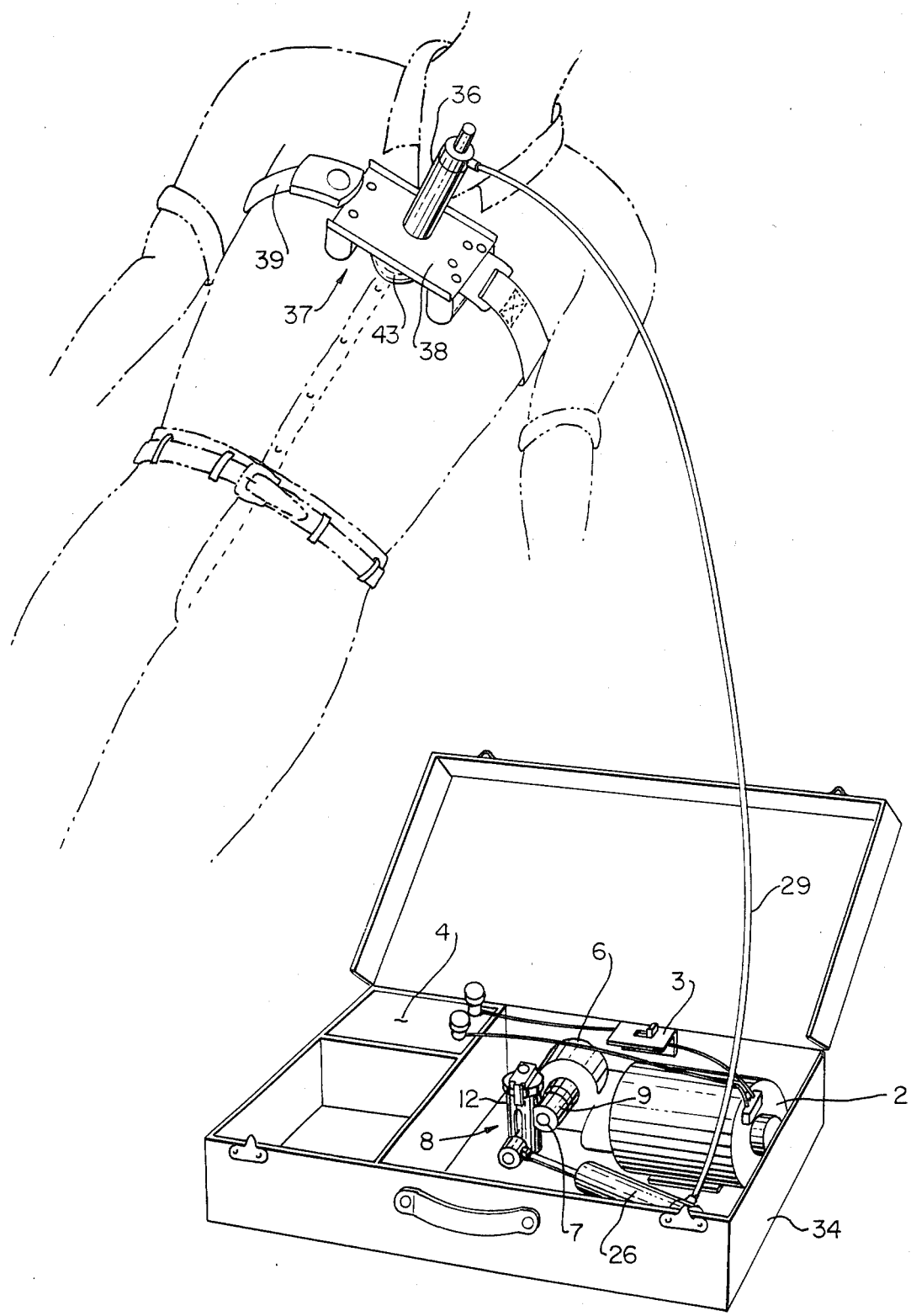
FIG. 1 is a perspective view illustrating the apparatus as it might be applied to an adult victim to impose chest compression and heart massage.

In terms of greater detail, and referring to FIG. 1, the heart massage apparatus of the invention comprises an electric motor 2, preferably of a type that will operate on either AC or DC power. The motor is appropriately connected through a switch 3 to a battery pack 4 for operation in a DC mode. The motor is connected to a gear reduction unit 6 which functions to convert the relatively high revolutions per minute and low torque of the motor into low RPM and high torque on the drive shaft 7. In the assembly illustrated, the gear reduction and motor speed are selected to provide a rotational velocity to the drive shaft 7 of 60 RPM, this rotational velocity being compatible with a chest compression rate of 60 per minute applicable to most adults. It will of course be understood that other speeds may be selected, or control means such as a variable speed clutch (not shown) may be interposed between the motor and gear reduction to adjust the rotation of the drive shaft 7 to any desired speed.

Mounted on the drive shaft 7 for rotation therewith is an actuator and stroke control assembly designated generally by the numeral 8. This assembly includes a collar member 9 having a bore to snugly receive the drive shaft, which is keyed to the collar member so that the collar member and shaft will rotate in unison. The collar member 9 is integral with and forms a part of an elongated crank body 12 generally symmetrical about a longitudinal axis that is laterally offset from the axis of rotation of the shaft 7 and perpendicular thereto.

As seen in FIGS. 7 and 8, the crank body 12 includes an intermediate slide bearing portion 13 having a bore 14 therethrough extending longitudinally along the longitudinal axis of the crank body. At one end, the crank body 12 is provided with laterally spaced and oppositely positioned longitudinally extending integral retention plates 16, their end remote from the bearing portion 13 being connected by an apertured cross piece 17. At its opposite end, the crank body extends in two bifurcations or tines 18 which also extend longitudinally and are spaced apart transversely to provide slide bearing surfaces 19 on the inner surfaces of the tines.

The crank body 12 is configured to receive stroke adjustment and actuator member 21, one spindle portion 22 of which is threaded over a major portion of its length and is adapted to pass upwardly between the tines 19 and through the bore 14 in a loose sliding fit. Another portion 23 of the member 21 comprises a stub shaft integral adjacent one of its ends with one end of the spindle 22 and extending perpendicular thereto. The diameter of the stub shaft is such that it makes a snug sliding fit between the surfaces 19 of the tines 18 when the threaded spindle extends upwardly as shown in FIG. 6. In this relationship, the threaded spindle extends upwardly between the two retention plates 16, to threadably engage a thumb nut 24 captured in the space between the retention plates on the one hand, and between the body portion 12 and the apertured plate 17 on the other. It will thus be seen that as the thumb screw is rotated, the threaded spindle 22 will be translated axially but will not rotate because a portion of the shaft 23 at the union with the spindle lies between the tine surfaces 19, thus preventing rotation of the spindle.

It will thus be seen (FIG. 6) that the axis of the stub shaft 23 is parallel to but laterally offset from the axis of rotation of drive shaft 7. Since the crank body is fixed for rotation with the shaft 7, it follows that rotation of the tines 18 about the axis of drive shaft 7 causes the stub shaft 23 to travel in a circular path concentrically about the axis of rotation of the drive shaft 7. The diameter of the circular concentric path is dependent on the position of the stub shaft 23 along the bifurcated tines, controlled by rotation of thumb nut 24. Thus, the closer the stub shaft approaches the gore or union of the tines at the intermediate body 13, the smaller will be the diameter of the circular path it will follow. On the other hand, rotation of the thumb nut to place the stub shaft near the end of the tines remote from the intermediate body portion 13, the greater will be the diameter of the circular path. This adjustment of the stub shaft controls the length and repetition rate of the stroke of hydraulic master cylinder 26.

Hydraulic master cylinder 26 is preferably of the spring return type, i.e., having within the cylinder a piston (not shown) mounted on the end of ram 27. The spring (not shown) is positioned ahead of the piston and abuts the base member 28 of the assembly, which also provides an IN-OUT port to which is connected the hydraulic line 29. The end of ram 27 remote from the piston is rotatably connected to actuator stub shaft 23 by a head 31. As the crank body and shaft 23 rotate about the axis of rotation of main drive shaft 7, the crank action of the stub shaft 23 causes axial reciprocation of the ram shaft 27 as indicated by the arrows. To accommodate lateral displacement of the master cylinder 26 as the ram head 31 moves about its circular pattern, the base 28 of the master cylinder is pivotally connected by a pivot pin 32 to an anchor bracket 33 suitably fixed to the carrying case 34 within which the assembly discussed above is enclosed.

As illustrated in FIG. 1, the hydraulic line 29 is connected at one end to the IN-OUT port of master cylinder 26 and at its other end is connected to the IN-OUT port of "slave" hydraulic cylinder 36. The "slave" cylinder 36 is part of a chest plate assembly designated generally by the numeral 37, which includes the cylinder 36, a support plate 38 on which the cylinder 36 is mounted, a quick-release strap 39 adapted to encircle the body of the victim, as shown, in the chest area, and a pair of pads 41 secured to the underside of the support plate and adapted to rest on the victim's chest as shown.

The "slave" cylinder 36 is equipped with a ram 42 adapted to reciprocate to the same extent and at the same repetition rate as the ram 27 of the master cylinder 26. The ram 42 is provided on its free end with a pad or "shoe" 43 adapted to engage the victim's chest, specifically the sternum, approximately 1½ to 2 inches above the xiphoid, which is the lower tip of the sternum. Ideally, the pressure exerted by the shoe 43 is concentrated on the sternum and does not impose direct pressure on the ends of the ribs connected to the sternum. Thus, once properly located on the sternum, the shoe 43 is retained in proper position by the tension in strap 29 and the pressure imposed on the chest by the pads 41 spaced laterally on opposite sides of the shoe.

In operation, the pressure exerting ram 42 is extended to exert pressure when the master cylinder ram 27 is pushed into the cylinder 26 by rotation of the crank stub shaft 23. Hydraulic fluid ahead of the piston in the master cylinder is pressurized and, through hydraulic line 29, imposes hydraulic pressure behind the piston (not shown) contained in "slave" cylinder 36, and to which the ram 42 is connected. A spring (not shown) within the cylinder 36 is compressed as the piston advances under hydraulic pressure and assists in retracting the piston and ram 42 when the pressure is relieved by retraction of the ram 27 of the master cylinder.

There will be times when it will be necessary to apply either mouth-to-mouth breathing to the victim or connect the victim to an artificial breathing apparatus, such as a mechanical respirator. To facilitate actuation of a mechanical respirator, the portable heart massage apparatus of this invention provides a power take-off designated generally by the numeral 44 and illustrated in FIG. 5. As there shown, the power shaft 7 of the gear reduction unit 6 extends in a stub shaft 46 on which is fixed a collar 47 having a cam plate 48 fixed thereto. As the shaft 46 rotates, the cam 48 also rotates, thus providing a cam surface or lobe 49 available to actuate an associated mechanical respirator (not shown).

It will thus be seen that in a relatively small carrying case, all the apparatus is present to administer heart massage to a victim. The apparatus is ready for use in an instant, and may be applied to a victim quite easily and rapidly. The apparatus, once started, will operate unattended, freeing the rescuers to provide other ministrations, or to observe the victim, without the distraction of having to manually administer the heart massaging chest compressions. When the victim's heart resumes beating on its own, the strap 29 may be loosened but the chest plate assembly 37 left in position for resumption of heart massage should that become necessary. Because of the lightness of the chest plate assembly, leaving the assembly loosely strapped on the victim, but inoperative, does not impose undue discomfort on the victim while assuring the ability to respond rapidly if the need arises.

Having thus described the invention, what is believed to be new and novel and sought to be protected by letters patent of the United States is as follows:

1. A heart massage apparatus for application to a victim whose heart has stopped beating and adapted to impose in a predetermined timed sequence pressure on the sternum of the victim sufficient to periodically compress the chest of the victim to thereby compress the heart between the sternum and backbone of the victim, comprising:
   (a) means generating a source of periodic pressure sufficient when applied to the sternum of the victim to compress the chest sufficiently to thereby compress the heart of the victim between the sternum and the backbone of the victim; and
   (b) means adapted to be attached to the chest of the victim cooperating with said means for generating periodic pressure to periodically apply in a timed sequence sufficient pressure on the sternum of the victim to periodically compress the victim's chest whereby the victim's heart is periodically compressed between the victim's sternum and backbone;
   (c) said means for generating periodic pressure including an electric motor, a gear reduction unit driven by said motor and providing a high torque low RPM power shaft, an actuator control assembly mounted on said power shaft and rotatable therewith and providing a crank shaft adapted to rotate in a circular path about the power drive shaft, a master hydraulic cylinder having a reciprocable hydraulic ram one end of which is pivotally connected to said crank shaft, said hydraulic ram generating periodic hydraulic pressure in said master hydraulic cylinder when said ram is reciprocated, and means connecting said master hydraulic cylinder to said means adapted to be attached to the chest of the victim whereby the pressure generated by said master cylinder is effective to compress the victim's chest.

2. A heart massage apparatus for application to a victim whose heart has stopped beating and adapted to impose in a predetermined timed sequence pressure on the sternum of the victim sufficient to periodically compress the chest of the victim to thereby compress the heart between the sternum and backbone of the victim, comprising:
   (a) means generating a source of periodic pressure sufficient when applied to the sternum of the victim to compress the chest sufficiently to thereby compress the heart of the victim between the sternum and the backgone of the victim; and
   (b) means adapted to be attached to the chest of the victim cooperating with said means for generating periodic pressure to periodically apply in a timed sequence sufficient pressure on the sternum of the victim to periodically compress the victim's chest whereby the victim's heart is periodically compressed between the victim's sternum and backbone;
   (c) said means for generating periodic pressure including a motor having a drive shaft, a master hydraulic cylinder having a pressure ram reciprocable therewithin, and means opertively interposed between said motor shaft and said master cylinder for effecting controlled reciprocation of the ram in a predetermined timed sequence;
   (d) said means operatively interposed between said motor shaft and said master cylinder comprising an actuator and stroke control assembly including a crank body generally symmetrical about a longitudinal axis that is laterally offset from the axis of rotation of said drive shaft and perpendicular thereto, a slide bearing portion on said crank body, a pair of spaced tines on said crank body, a stroke adjustment member mounted on said crank body, said stroke adjustment member having a threaded spindle slidably mounted in said slide bearing portion for selective adjustment in relation to said crank body, a crank shaft integral with said threaded spindle and slidably disposed between said tines, means on said crank body selectively manipulable to adjust the position of said crank shaft in relation to the axis of rotation of said motor shaft, and means pivotably connecting said crank shaft to said pressure ram of said master cylinder whereby rotation of said crank shaft about the axis of rotation of said motor drive shaft effects reciprocation of said master cylinder ram through a selectively variable stroke.

* * * * *